United States Patent [19]

Miller et al.

[11] Patent Number: 5,137,527
[45] Date of Patent: Aug. 11, 1992

[54] ENTERAL-SPECIFIC SPIKE/BAG PORT SYSTEM

[75] Inventors: Robert A. Miller, Crystal Lake; Michael Becker, Palatine; Jerre Kachmar, Grayslake; Algirdas J. Bindokas, Clarendon Hills; Richard A. Rollins, Mundelein, all of Ill.

[73] Assignee: Clintec Nutrition Co., Deerfield, Ill.

[21] Appl. No.: 585,818

[22] Filed: Sep. 20, 1990

[51] Int. Cl.⁵ .............................................. A61M 25/00
[52] U.S. Cl. .................................. 604/415; 215/247; 604/411; 604/905
[58] Field of Search ............................. 604/408–416, 604/905, 256; 215/31

[56] References Cited

U.S. PATENT DOCUMENTS

| | | |
|---|---|---|
| 4,078,699 | 3/1978 | Soto . |
| 4,150,673 | 4/1979 | Watt . |
| 4,187,893 | 2/1980 | Bujan . |
| 4,201,406 | 5/1980 | Dennehey et al. . |
| 4,303,067 | 12/1981 | Connolly et al. . |
| 4,336,802 | 6/1982 | Stone et al. . |
| 4,592,092 | 5/1986 | McPhee ............................ 604/415 X |
| 4,632,673 | 12/1986 | Tiitola et al. ...................... 604/415 |
| 4,636,204 | 1/1987 | Christopherson et al. ........... 604/283 |
| 4,836,397 | 6/1989 | Fowles ............................. 604/415 X |
| 4,889,256 | 12/1989 | Fowles ............................. 220/306 |
| 4,892,222 | 1/1990 | Schmidt et al. .................. 604/415 X |
| 4,935,010 | 6/1990 | Cox et al. ........................ 604/122 |
| 4,973,328 | 11/1990 | Smith ............................. 604/411 |
| 4,998,927 | 3/1991 | Vaillancourt ...................... 604/283 |

FOREIGN PATENT DOCUMENTS

| | | |
|---|---|---|
| 0136848 | 8/1986 | European Pat. Off. . |
| 0200483 | 5/1987 | European Pat. Off. . |
| 830222 | 3/1960 | United Kingdom . |

Primary Examiner—Robert A. Hafer
Assistant Examiner—Kerry Owens
Attorney, Agent, or Firm—Hill, Van Santen, Steadman & Simpson

[57] ABSTRACT

A port/spike assembly including an enteral spike having a diameter substantially less than the diameter of a standard parenteral spike. The assembly also includes a port having a tube with an outer wall which defines a generally cylindrical elongated bore. A frangible membrane is disposed inside the elongated bore, and divides the bore into upper and lower bore sections. A selector ring is provided in the upper bore section for permitting insertion of the reduced diameter enteral spike and for preventing the insertion of a standard parenteral spike through the membrane. The assembly prevents inadvertent insertion of a parenteral spike into an enteral feeding system.

20 Claims, 1 Drawing Sheet

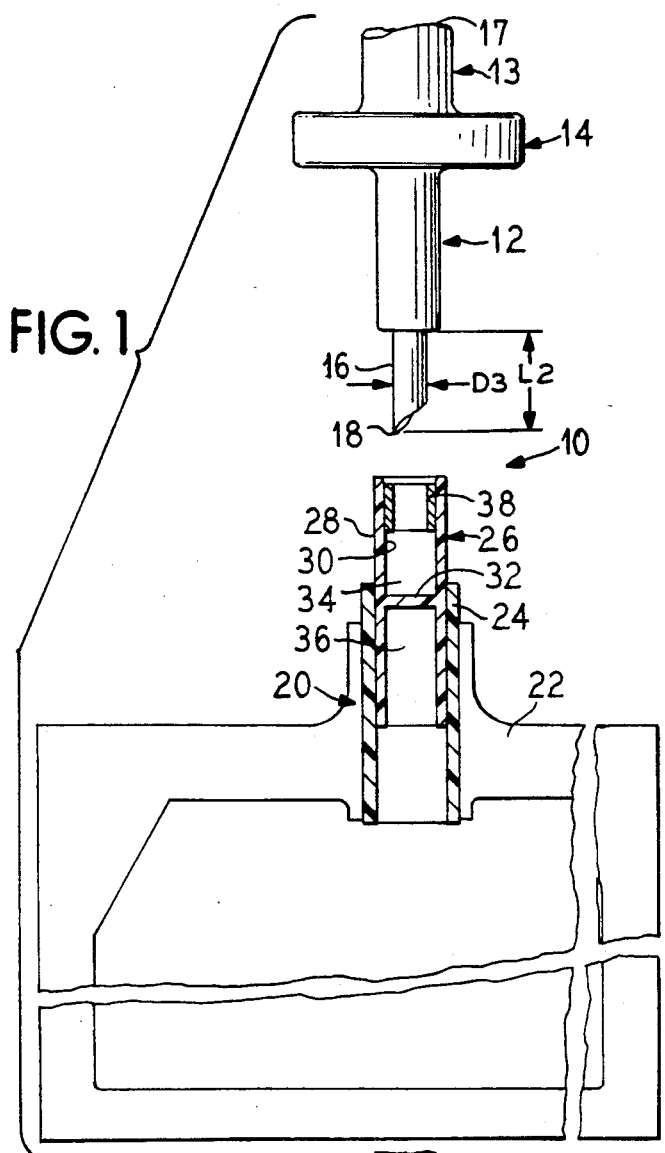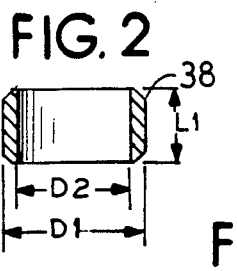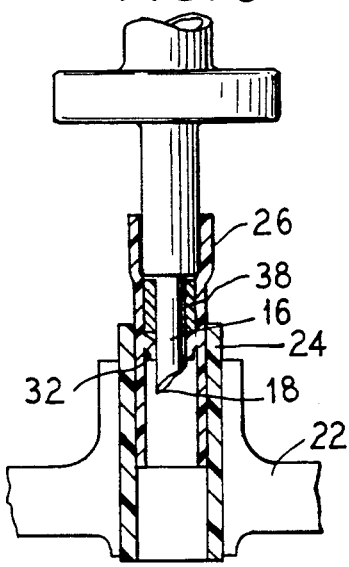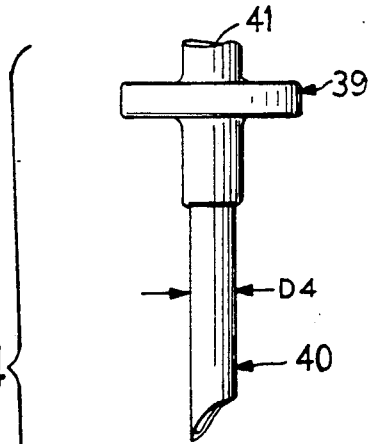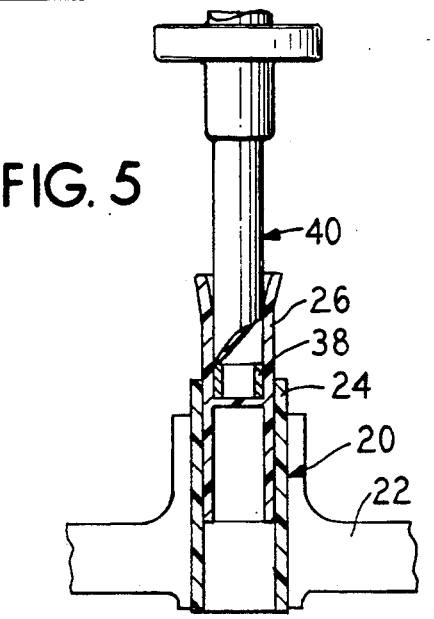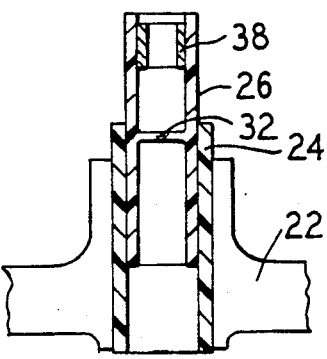

ENTERAL-SPECIFIC SPIKE/BAG PORT SYSTEM

BACKGROUND OF THE INVENTION

The present invention relates to a port assembly for an enteral feeding bag. In particular, the present invention relates to a port assembly that prevents the insertion of a spike of a parenteral set, while permitting insertion of a spike of an enteral set, into an enteral container.

Collapsible containers for the administration of medical solutions are well known. An example of such a container is the VIAFLEX® container marketed by Baxter Healthcare Corporation, Deerfield, Illinois. Typically, the containers, also known as "bags", include a port that provides access to the material packaged within the bag. The port includes a tubular structure defining an inner bore. Located within the inner bore is a frangible membrane that provides a barrier between the material (usually a fluid) contained within the bag and the outside environment.

Spikes are used to pierce the frangible membrane and gain access to the fluid within the bag. The spikes are typically part of a set that allows the infusion of the product within the container to a patient.

Such collapsible containers or bags are typically used, in the medical field, for administering parenteral solution, peritoneal dialysis solutions, and enteral feeding compositions. "Parenteral" refers to the infusion of a product intravenously, while "enteral" refers to infusion of the product into the gut, typically through a tube inserted through the nose and into a patient's stomach. Although it is not uncommon that the bags used in enteral and parenteral systems are similar, the functions of the fluids employed in the respective systems are not. Indeed, in many instances, if a solution intended for enteral infusion was mistakenly introduced into a patient parenterally, serious harm to the patient could result.

SUMMARY OF THE INVENTION

The present invention provides a port/spike assembly that includes an enteral spike having a diameter substantially less than the diameter of a standard parenteral spike. The assembly also includes a port including a membrane tube having an outer wall which defines a generally cylindrical elongated bore. A frangible membrane is disposed inside the bore and divides the bore into upper and lower bore sections. A selector ring is provided in the upper bore section for permitting insertion of the reduced diameter standard parenteral spike through the membrane.

In an embodiment, the ring may be constructed from a rigid polypropylene or polyethylene and the bag is constructed from a polyvinyl chloride resin or polyolefin resin.

The present invention also provides a container that will only accept an enteral set and prevents a parenteral set from accessing the container.

Accordingly, it is an advantage of the present invention to provide a port/spike assembly that prevents the inadvertent insertion of a parenteral spike into an enteral feeding system.

An additional advantage of the present invention is that a selector ring is provided that can be inserted into a standard port allowing the port to be adapted to only receive an enteral set.

A further advantage of the present invention is that it overcomes the disadvantages of the prior art with minimum piece part and tooling costs.

Additional features and advantages are described in, and will be apparent from, the detailed description of the presently preferred embodiments and from the drawings.

BRIEF DESCRIPTION OF THE DRAWINGS

FIG. 1 illustrates an exploded view illustrating an embodiment of the port/spike assembly of the present invention.

FIG. 2 illustrates a sectional view of the selector ring of the present invention.

FIG. 3 illustrates a sectional view of the port/spike assembly of FIG. 1 in an installed position.

FIG. 4 illustrates an exploded view of a standard parenteral spike and the port of the present invention.

FIG. 5 illustrates a sectional view of the components shown in FIG. 4 with an attempted insertion of a standard parenteral spike into the port of the present invention.

DETAILED DESCRIPTION OF THE PRESENTLY PREFERRED EMBODIMENTS

The present invention provides a port/spike assembly for an enteral bag that prevents the inadvertent insertion of a parenteral spike, and thereby a parenteral set, into the port of an enteral container. The present invention prevents the inadvertent infusion of an enteral solution parenterally into a patient.

Referring now to the Figures, FIG. 1 illustrates an embodiment of the port/spike assembly 10 of the present invention. The assembly 10 includes a set 13 having a spike 12 including a mounting section 14 and a piercing section 16. A point 18 is formed at the terminal end of the piercing section 16.

The set 13 functions to access a container 22 allowing the infusion of the contents of the container into a patient. To this end, the spike 12 is connected by the mounting section 14 to a flexible hollow tube 17. The flexible hollow tube 17 is in fluid communication with, for example, an enteral feeding tube (not shown) that allows the contents of the container to be infused into the stomach of a patient.

The set 13, and specifically the spike 12, is designed to be received within a port 20 mounted on a container 22. The container 22 can be made from a variety of materials including polyvinyl chloride resin. The port 20 includes a port tube 24 that is in fluid communication with an interior of the container 22.

In the embodiment of the port 20 illustrated, a membrane tube 26 is disposed inside, and coaxial with, the port tube 24. The membrane tube 26 includes an outer wall 28 defining a generally cylindrical elongated bore 30. A frangible membrane 32 divides the elongated bore 30 into an upper bore section 34 and a lower bore section 36.

Pursuant to the present invention, a selector ring 38 is disposed within the upper bore section 34 of the elongated bore 30 of the membrane tube 26. The selector ring 38 is generally annular, and can be made from a variety of materials such as, for example, rigid polypropylene.

As illustrated in FIG. 2, the selector ring 38 has an outer diameter D1 that allows the selector ring 38 to be interference-fitted within the elongated bore 30 of the membrane tube 26. Of course, if desired, the selector ring 38 can be sealed within the bore 30 of the membrane tube 26. For example, the selector ring 38 can be sonically welded within the membrane tube 26. However, as illustrated in FIGS. 3 and 5, preferably, the ring 38 is displaceable within the upper bore 34.

The selector ring 38 has an inner diameter D2 that is larger than the outer diameter D3 of a piercing section 16 of the spike 12 of an enteral set. The selector ring 38 has a length L1 that is less than the length L2 of the piercing section 16. In an embodiment that has been found to function satisfactorily, L1 is approximately 0.15 inches, D1 is approximately 0.2 inches, and D2 is approximately 0.14 inches.

Referring now to FIG. 3, the insertion of the spike 12 of an enteral set 13 into the port 20 of the present invention is illustrated. The diameter D2 and D3 of the selector ring 38 and spike 12, respectively, are chosen so that the selector ring 38 permits the passage of the piercing section 16. This allows the point 18 to pierce the frangible membrane 32, thus permitting fluid communication between the spike 12 and enteral set 13 and the interior of the bag 22. Accordingly, the enteral set 13 is allowed to access the container and thereby infuse the solution housed within the container into a patient.

FIGS. 4 and 5 illustrate a standard parenteral set 39 including spike 40. The parenteral set 39 includes a spike 40, for accessing a container, and flexible tube 41 for communicating fluid within the container to a cannula (not shown) or other means for infusing a fluid intravenously into a patient.

As illustrated, the diameter D4 of the spike 40 of the parenteral set 39 is substantially greater than the inner diameter D2 of the selector ring 38. If a medical personnel inadvertently attempts to insert the parenteral set spike 40 into the port 20 of the enteral container 22, as illustrated in FIG. 5, the spike 40 will contact the selector ring 38 located above the frangible membrane 32. Although, the selector ring 38 may be displaced downwardly toward the frangible membrane 32 by the spike 40, the selector ring 38 prevents the spike 40 from piercing the frangible membrane 32.

Accordingly, the present invention prevents a parenteral set 39 and spike 40 from piercing the membrane 32 of an enteral container 22 and accessing the solution in the container. Thus, the accidental introduction of an enteral fluid parenterally is avoided.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A port/spike fluid connection assembly for the administration of an enteral product comprising:
    an enteral set having a spike with a diameter substantially less than a diameter of a standard parenteral set spike;
    a port including an elongated tube, with a frangible membrane disposed inside a bore of the tube and dividing the bore into an upper bore and a lower bore; and
    means, in the upper bore, for permitting the enteral set spike to pierce the membrane and preventing the standard parenteral set spike from piercing the membrane, the means being slidably movable from a first position located at a top of the upper bore to a second position located near the frangible member.

2. The port/spike assembly of claim 1 wherein said means includes a member having an outer diameter corresponding to an inner diameter of the bore, and an inner diameter smaller than a diameter of the standard parenteral set spike, but larger than a diameter of said enteral set spike.

3. The port/spike assembly of claim 2 wherein the member is an annular ring.

4. The port/spike assembly of claim 1 wherein said means comprises a rigid polypropylene annular ring secured within the bore.

5. The port/spike assembly of claim 2 wherein the member has a length that is less than a length of the spike of the enteral set.

6. The port/spike assembly of claim 1 wherein said means is interference fitted into said bore.

7. The port/spike assembly of claim 1 wherein said means is displaceable within the upper bore.

8. A container for housing fluid that is not infused intravenously comprising:
    a port including an elongated tube defining a generally cylindrical elongated bore having a length and a frangible membrane disposed inside the tube dividing the elongated bore into upper and lower bore sections; and
    a selector ring, in said upper bore section, for preventing insertion of a spike from a parenteral set through said membrane, said ring having a diameter that is less than the diameter of the spike of the parenteral set, the selector ring being movable along the length of the elongated bore, during insertion of the spike, from a first position to a second position wherein the selector ring is located in juxtaposition to the frangible membrane.

9. The container of claim 8 wherein the selector ring means is interference fitted within the 10. The container of claim 8 wherein the selector ring has a length that is less than a length of a spike of an enteral set.

11. The container of claim 8 wherein the selector ring has an outer diameter of approximately 0.2 inches, an inner diameter of approximately 0.14 inches, and a length of approximately 0.15 inches.

12. The container of claim 8 wherein the selector ring is displaceable within said upper bore section.

13. The container of claim 8 wherein the selector ring has an outer diameter corresponding to an inner diameter of the bore, and an inner diameter smaller than a diameter of the parenteral spike, but larger than a diameter of an enteral spike.

14. An enteral set and container comprising:
    an enteral set having a spike with a diameter substantially less than a diameter of a spike of a standard parenteral set;
    an enteral container including a port including an elongated bore having a length, with a frangible membrane disposed inside the elongated bore and dividing the bore into upper and lower bore sections; and
    an annular ring, in the upper bore section, for permitting the spike of the enteral set to pierce the membrane and preventing the spike of the standard parenteral set from piercing the membrane, the ring being movable along the length of the elongated bore, during insertion of the spike, from a first position to a second position located in juxta-position to the frangible membrane.

15. The enteral set and container of claim 14 wherein the annular ring includes an outer diameter corresponding to an inner diameter of the bore, and an inner diameter smaller than a diameter of the spike of the standard parenteral set, but larger than a diameter of the spike of the enteral set.

16. The enteral set and container of claim 14 wherein the annular ring has a length that is less than a length of the spike of the enteral set.

17. The container of claim 14 wherein the selector ring is displaceable within the upper bore section.

18. A method for providing an enteral solution for infusion into a patient including the steps of:

providing an enteral set having a spike having a diameter substantially less than a diameter of a standard parenteral spike;

providing an enteral container with a port including a tube having an inner bore divided into upper and lower bore sections by a frangible membrane;

providing a ring having an outer diameter corresponding to an inner diameter of the bore, and an inner diameter larger than the diameter of the enteral spike but smaller than the diameter of the parenteral spike;

placing said ring into the upper bore section of said membrane tube; and allowing the ring to move along a length of the upper bore section, as a spike is received within the port, from a first position to a second position located in juxtaposition to the frangible membrane.

19. The method of claim 18 including the step of inserting the enteral spike through the frangible membrane.

20. The method of claim 18 including the step of allowing the ring to be displaced by the insertion of the parenteral spike but preventing the parenteral spike from piercing the membrane.

* * * * *